United States Patent
Fulmer et al.

(12) 
(10) Patent No.: US 6,573,408 B1
(45) Date of Patent: Jun. 3, 2003

(54) SYSTEM AND METHOD FOR PURIFYING CUMENE HYDROPEROXIDE CLEAVAGE PRODUCTS

(75) Inventors: John William Fulmer, Mt. Vernon, IN (US); Pramod S. Kumbhar, Bangalore (IN); Marakani Venkata Ramani, Bangalore (IN); Bharat Singh, Bangalore (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/683,190

(22) Filed: Nov. 29, 2001

(51) Int. Cl.⁷ .................. C07C 45/00; C07C 41/00; C07C 43/02; C07C 37/68; C07C 37/08
(52) U.S. Cl. .................. 568/383; 568/449; 568/741; 568/742; 568/754; 568/798
(58) Field of Search ................... 568/383, 649, 568/741, 742, 754, 798

(56) References Cited

U.S. PATENT DOCUMENTS

| | | |
|---|---|---|
| 2,734,085 A | 2/1956 | Adams et al. |
| 2,744,143 A | 5/1956 | Filar |
| 2,992,169 A | 7/1961 | Gregory et al. |
| 3,335,070 A | 8/1967 | Adams |
| 3,437,699 A | 4/1969 | Flickinger |
| 3,454,653 A | 7/1969 | Larson |
| 3,692,845 A | 9/1972 | Cheema et al. |
| 3,862,244 A | 1/1975 | Genod et al. |
| 3,931,339 A | 1/1976 | Cooke |
| 3,965,187 A | 6/1976 | Little et al. |
| 4,092,360 A | 5/1978 | Van Peppen et al. |
| 4,298,765 A | 11/1981 | Cochran et al. |
| 4,334,107 A | 6/1982 | Van Peppen |
| 4,973,766 A | 11/1990 | Penzo et al. |
| 5,262,016 A | 11/1993 | Lorenzoni et al. |
| 5,264,636 A | 11/1993 | Shirahata et al. |
| 5,414,154 A | 5/1995 | Jenczewski et al. |
| 5,491,268 A | 2/1996 | Cipullo |
| 5,502,259 A | 3/1996 | Zakoshansky et al. |
| 5,510,543 A | 4/1996 | Fulmer et al. |
| 6,066,767 A | 5/2000 | Zakoshansky et al. |

*Primary Examiner*—Samuel Barts
*Assistant Examiner*—Sikarl A. Witherspoon

(57) ABSTRACT

A system for purifying a cumene hydroperoxide cleavage product mixture comprises a cumene hydroperoxide cleavage product mixture feed containing impurities in fluid communication with an aqueous alkaline solution feed; the cumene hydroperoxide cleavage product mixture and aqueous alkaline solution feeds are in fluid communication with a neutralization drum having an aqueous salt phase outlet; an aqueous salt phase feed containing impurities in fluid communication with a heat treatment vessel having a heat-treated aqueous salt phase outlet; and a heat-treated aqueous salt phase feed containing water-soluble derivatives of the impurities in fluid communication with the cumene hydroperoxide cleavage product mixture prior to the neutralization drum.

26 Claims, 1 Drawing Sheet

SYSTEM AND METHOD FOR PURIFYING CUMENE HYDROPEROXIDE CLEAVAGE PRODUCTS

BACKGROUND OF INVENTION

This disclosure relates to methods for phenol production and, more particularly, to systems and methods for purifying cumene hydroperoxide cleavage products.

Processes for preparing phenol are well known. The cumene method comprises two stages: the first one is cumene oxidation by air oxygen to cumene hydroperoxide (CHP), and the second one is CHP acidic catalytic cleavage (decomposition) to phenol and acetone. After producing and cleaving cumene hydroperoxide (CHP), the resultant cumene hydroperoxide cleavage product mixture contains phenol and acetone as the principal products together with varying amounts of impurities, e.g., alpha-methylstyrene, acetophenone, mesityl oxide, cumene, acetaldehyde, hydroxyacetone, and residual acid catalyst, e.g., sulfuric acid catalyst. Before the products can be recovered it is necessary to remove or neutralize the acid catalyst in the CHP cleavage product mixtures since the presence of the acid catalyst in the subsequent distillation interferes with efficient recovery of the product and by-products of the reaction, in addition to causing corrosion of the distillation equipment.

Commercially, the residual sulfuric acid catalyst present in the cleavage product mixture is neutralized with an aqueous alkaline solution, e.g., aqueous sodium hydroxide. The resulting concentrated aqueous sodium sulfate salt solution formed from the sulfuric acid and the sodium hydroxide reaction is then separated from the main organic mixture using a series of liquid-liquid extraction operations. The resulting organic mixture, now free of sulfuric acid, is then subjected to a series of fractional distillations to recover the products and various components.

U.S. Pat. Nos. 2,734,085; 2,744,143; 3,931,339; and 5,510,543 variously teach conducting the cleavage acid extraction/neutralization step as a liquid-liquid extraction process in a reactor utilizing a circulating aqueous solution of concentrated sodium sulfate salt, i.e., the extractant, formed in situ by the reaction of sodium hydroxide and sulfuric acid. It is known that hydroxyacetone is typically present in an amount of 1,200–2,200 parts per million (ppm) concentration in the CHP cleavage product mixture prior to neutralization. During neutralization the hydroxyacetone equilibrates and partitions into two phases (organic and aqueous) within the neutralizer vessel in about equal concentrations. Hydroxyacetone is particularly troublesome to remove from phenol as it co-distills with phenol during the downstream rectification processes and contaminates the final phenol product. Although hydroxyacetone may be present in only minute quantities in the final phenol product, the hydroxyacetone impurity has color-forming tendencies and its presence renders the phenol product quality unacceptable for many end use applications, such as bisphenol A and polycarbonate.

To prevent this, U.S. Pat. Nos. 3,335,070; 3,454,653; 3,692,845; 5,502,259; and 6,066,767 variously teach removing hydroxyacetone from phenol via condensation reactions and conversion to higher boiling point materials, which create by-products that can be more easily separated from phenol in subsequent distillation steps. Both homogeneous and heterogeneous processes are described which use both basic and acidic treating agents on the organic streams to promote hydroxyacetone condensation reactions, such as sodium hydroxide, amines, ion exchange resins and zeolites. However, this treatment method is only partially effective because a new impurity 2-methybenzofuran (2MBF) forms, which is also very difficult to remove from phenol by distillation. This problem is particularly troublesome as its presence also renders the phenol product quality unacceptable for many end use applications.

In the conversion of hydroxyacetone to higher boiling point materials, U.S. Pat. No. 6,066,767 ('767 patent) describes a process for purifying phenol using sodium hydroxide and alkaline agents as treatment agents to promote deep condensation reactions of hydroxyacetone to high boiling point materials purportedly free of 2MBF. In this process the CHP cleavage product mixture is extracted with 10–20 weight percent (wt. %) sodium sulfate salt solution according to conventional methods, and the hydroxyacetone contained within the aqueous salt phase is treated with sodium hydroxide reagent to form deep condensation products which recycle into the process and mix with the phenol-acetone stream for later removal.

Several drawbacks are associated with the method of the '767 patent. First, there are high raw material costs associated with the neutralizing reagents. In the '767 method, to effectively neutralize the acidic 10–20 wt. % sodium sulfate aqueous stream large quantities of sodium hydroxide must be added to neutralize and maintain the excess alkalinity required to provide catalysis. In response to this quantity of sodium hydroxide additional sulfuric acid must be purchased and utilized to neutralize the sodium hydroxide so as to maintain the critical pH control range while neutralizing the CHP cleavage product mixture. Thus raw material costs are significant for the '767 process.

Secondly, alkaline phenol salts (e.g., sodium phenolate) form, which can cause pH fluctuations, incomplete phase separations during neutralization, and contribute to downstream fouling of equipment. If the alkaline phenol salts cause pH fluctuations, and the critical pH control range cannot be maintained, emulsions may form and render various equipment useless. Third, the '767 patent acknowledges that unidentified deep condensation products formed from hydroxyacetone re-enter the organic stream and recycle into the process. These unknown condensation products can potentially contaminate the final phenol product and risk causing other quality and equipment problems. Fourth, the process disclosed in the '767 patent employs multiple extraction stages to optimize the removal of hydroxyacetone. These multiple extraction stages require additional time, labor, materials and equipment to implement, thus increasing costs to remove hydroxyacetone to acceptable levels in the final phenol product.

Accordingly there remains a need in the art for a method and system for removing hydroxyacetone and other impurities from cumene hydroperoxide cleavage products to acceptable levels.

SUMMARY OF INVENTION

A method for removing impurities from a cumene hydroperoxide cleavage product mixture comprises heating an aqueous salt phase containing impurities at a temperature and for a time sufficient in a non-alkaline environment to form water-soluble derivatives of the impurities; combining the aqueous salt phase containing the water-soluble derivatives with a cumene hydroperoxide cleavage product mixture to form a combined product mixture; and separating the aqueous salt phase containing the water-soluble derivatives of the impurities from the combined product mixture.

In another embodiment, the method for removing impurities from a cumene hydroperoxide cleavage product mixture comprises heating an aqueous salt phase containing impurities at a temperature and for a time sufficient to form water-soluble derivatives of the impurities, wherein heating comprises heating the aqueous salt phase containing the impurities at a temperature of about 150 to about 350° Celsius for about 0.5 to about 1.5 hours under a pressure of about 50 to about 1 500 pounds per square inch to the reaction mixture; combining the aqueous salt phase containing the water-soluble derivatives with a cumene hydroperoxide cleavage product mixture to form a combined product mixture; and separating the aqueous salt phase containing the water-soluble derivatives of the impurities from the combined product mixture.

A system for purifying a cumene hydroperoxide cleavage product mixture comprises means for heating an aqueous salt phase containing impurities at a temperature and for a time sufficient to form water-soluble derivatives of the impurities; means for combining the aqueous salt phase containing the water-soluble derivatives with a cumene hydroperoxide cleavage product mixture to form a combined product mixture; and means for separating the aqueous salt phase containing the water-soluble derivatives of the impurities from the combined product mixture.

In another embodiment, the system for purifying a cumene hydroperoxide cleavage product mixture comprises a cumene hydroperoxide cleavage product mixture feed containing impurities in fluid communication with an aqueous alkaline solution feed; the cumene hydroperoxide cleavage product mixture and aqueous alkaline solution feeds are in fluid communication with a neutralization drum having an aqueous salt phase outlet; an aqueous salt phase feed containing impurities in fluid communication with a heat treatment vessel having a heat-treated aqueous salt phase outlet; and a heat-treated aqueous salt phase feed containing water-soluble derivatives of the impurities in fluid communication with the cumene hydroperoxide cleavage product mixture prior to the neutralization drum.

BRIEF DESCRIPTION OF DRAWINGS

Referring now to the FIGURE, which is merely illustrative, wherein the like elements are numbered alike, the FIGURE is a schematic flow diagram illustrating an exemplary embodiment of a system and method for removing impurities from cumene hydroperoxide cleavage products.

DETAILED DESCRIPTION

Figure 1:
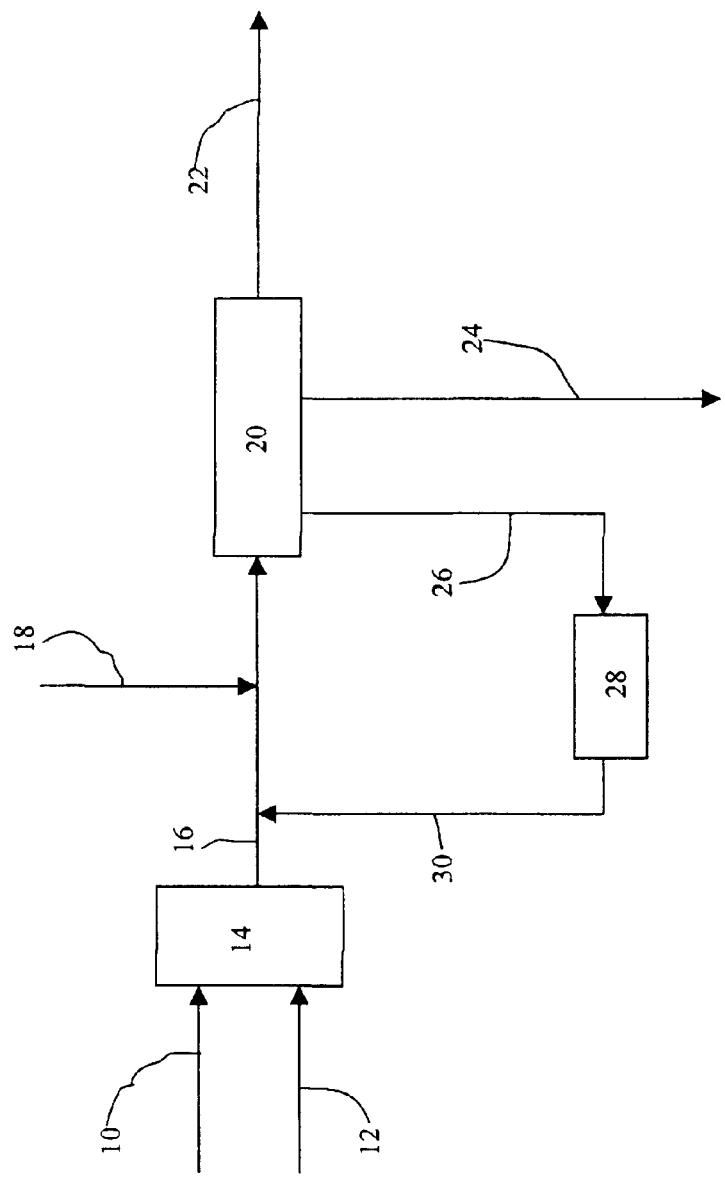

The inventors hereof have discovered that common impurities in phenol production can be converted to water-soluble derivatives by applying heat to the circulating aqueous salt phase stream. Quite unexpectedly, hydroxyacetone and aldehydes, e.g., acetaldehyde and propionaldehyde, present in this stream are effectively converted to water-soluble derivatives by the heat treatment in the absence of any additives or treatment agents. These water-soluble derivatives are not heavy condensation products or high boiling point materials that can further convert or react to form 2MBF in this environment. Instead, these water-soluble derivatives are extractable using existing equipment, and an additional heat treatment vessel. This heat treatment vessel eliminates the need for multiple extraction steps beyond existing equipment, and can be installed within existing facilities. Accordingly, the drawbacks of prior attempts employing condensation reactions and conversions to higher boiling point materials, and the like, are avoided or prevented by heat treating the circulating aqueous salt phase stream.

An efficient method and system for the commercial purification of CHP cleavage mixture products in phenol production comprises heating an aqueous salt phase containing impurities at a temperature and for a time sufficient to form water-soluble derivatives of the impurities; combining the aqueous salt phase containing the water-soluble derivatives with a cumene hydroperoxide cleavage product mixture to form a combined product mixture; and, separating the aqueous salt phase containing the water-soluble derivatives of the impurities from the combined product mixture. The method and system removes or eliminates impurities such as mesityl oxide, acetaldehyde, hydroxyacetone and various carbonyl-containing and aldehyde-containing impurities, and combinations comprising at least one of the foregoing impurities, to acceptable levels in the final phenol product. For purposes of illustration, the process will be discussed in the context of removing hydroxyacetone from CHP cleavage product mixtures. However, other by-products and impurities, such as those mentioned above can also be removed effectively using the method and system disclosed herein.

The FIGURE illustrates a flow chart showing in detail an embodiment of a system and method for removing hydroxyacetone from CHP cleavage product mixtures. A cumene hydroperoxide feed 10 ("CHP feed 10") and an acid catalyst feed 12, e.g., sulfuric acid, or other mineral acids, and the like, are fed into and mixed within a cumene hydroperoxide cleavage reactor 14 ("reactor 14") having a CHP cleavage product mixture outlet. A CHP cleavage product mixture feed 16 containing impurities exits reactor 14, flows downstream, and mixes with an aqueous solution of aqueous alkaline solution such as aqueous sodium hydroxide, and the like, (aqueous alkaline solution feed 18), prior to or when entering a neutralizer drum 20 ("drum 20") serially disposed after reactor 14, in an amount effective to neutralize any residual acid catalyst present and maintain the pH of the resultant neutralized cleavage product mixture within drum 20. The combined cleavage product mixture and aqueous alkaline solution feeds 16 and 18, respectively, comprise phenol, acetone, cumene, by-products and residual sulfuric acid, and an oxidized aqueous solution comprising about 10 to about 30 weight percent (wt. %) sodium sulfate solution containing water-soluble derivatives of impurities, which will be discussed below in further detail.

The amount of aqueous alkaline solution feed 18 may be controlled using a flow control device (not shown), e.g., a valve, that is actuated either manually or by an operator via an electronic interface (not shown), and may be optionally monitored using a sensor such as a pressure sensor, output sensor, flow rate sensor, mass flow sensor, and the like. Drum 20 contains an amount of aqueous alkaline solution effective to maintain the pH of the resulting neutralized cleavage product mixture at greater than or equal to about 1, preferably greater than or equal to about 3, most preferably greater than or equal to about 5; and, at a pH less than or equal to about 10, preferably less than or equal to about 7, most preferably less than or equal to about 6.

The neutralized cleavage product mixture may be allowed to settle within drum 20, forming two distinct phases, a top organic phase and a bottom aqueous salt phase. The organic phase comprises phenol, acetone, cumene, mesityl oxide, alphamethylstyrene, acetophenone, dimethylbenzyl alcohol, cumylphenol, hydroxyacetone, various trace carbonyls and dissolved water, while the aqueous salt phase comprises about 10 to about 30 wt. % sodium sulfate solution (formed in situ within drum 20), preferably about 10 to about 25 wt. % sodium sulfate solution, containing impurities including but not limited to hydroxyacetone and acetaldehyde. Drum 20 includes an aqueous salt phase outlet, an aqueous salt phase purge outlet, and a neutralized cleavage product outlet, whereby the organic phase containing the neutralized cleavage product exits that outlet as neutralized cleavage product stream 22. The resultant product stream undergoes an extraction step wherein phenol and acetone are extracted using conventional techniques known to one skilled in the art. A portion of the aqueous salt phase containing undesired impurities is purged from drum 20 as an aqueous salt phase purge 24, while the remaining aqueous salt phase proceeds downstream as an aqueous salt phase stream 26 to a heat treatment vessel 28 ("heat treatment vessel 28"), having a heat-treated aqueous salt phase stream outlet, and serially disposed after and in fluid communication with drum 20. Heat treatment vessel 28 is in fluid communication and serially disposed after, preferably in a continuous loop, with drum 20. The continuous loop comprises a continuous flow beginning from CHP cleavage product mixture feed 16 to drum 20, aqueous salt phase stream 26, heat-treated aqueous salt phase stream 30 and returning to CHP cleavage product mixture feed 16. The concentration(s) of one or more impurities, e.g., hydroxyacetone, present in the aqueous salt phase stream 26 can be measured using quantitative analysis techniques, e.g., gas chromatography methods utilizing a Hewlett Packard gas chromatograph.

Once aqueous salt phase stream 26 enters heat treatment vessel 28, vessel 28 is maintained at a temperature sufficient to convert the impurities to their water-soluble derivatives. To achieve such conversion heat treatment vessel 28 is maintained at a lower temperature of about 150 degrees Celsius (° C.), preferably about 170° C., most preferably about 200° C., to an upper temperature of about 350° C., preferably about 330° C., most preferably about 300° C., or a temperature range of about 200° C. to about 300° C., and at a lower pressure of about 50 pounds per square inch (psi), preferably about 100 psi, most preferably about 200 psi, to an upper pressure of about 1500 psi, preferably about 1400 psi, most preferably about 1300 psi, or a pressure range of about 200 to about 1300 psi. The pH is monitored and controlled for heat treatment vessel 28, and may be controlled by the amount of aqueous alkaline solution fed upstream. More particularly, vessel 28 contains an amount of aqueous alkaline solution effective to maintain the pH of the resulting neutralized cleavage product mixture at greater than or equal to about 3, preferably greater than or equal to about 4; and, at a pH less than or equal to about 6, preferably less than or equal to about 5.

The rate of decomposition, or percent conversion, of hydroxyacetone to water-soluble derivatives can also be monitored, e.g., by quantitatively measuring the hydroxyacetone content of heat-treated aqueous salt phase stream 30 using ion exclusion chromatography techniques, e.g., utilizing a DX100 Ion Chromatograph commercially available from Dionex Corporation, Sunnyvale, Calif. The amount of hydroxyacetone present in heat-treated aqueous salt phase stream 30 is compared with the amount of hydroxyacetone present in neutralized aqueous salt phase stream 26 to determine whether the desired percent conversion of hydroxyacetone to water-soluble oxidized hydroxyacetone derivatives is being achieved. The rate of decomposition, or conversion, can be optimized by varying certain operating conditions such as the aqueous salt phase stream circulation rate, aqueous salt phase stream residence time within heat treatment vessel 28, temperature, pressure, and the like. The desired percent conversion of hydroxyacetone to oxidized hydroxyacetone derivative is greater than about 50 percent, preferably greater than about 80 percent, most preferably greater than about 90 percent.

The resultant heat-treated aqueous salt phase stream 30 exiting vessel 28 generally comprises about 10 to about 30 wt. % sodium sulfate solution containing the water-soluble derivatives. To effectively maintain the pH within neutralizer drum 20 the aqueous salt phase stream 30 preferably combines with CHP cleavage product mixture feed 16 prior to entering drum 20. The resultant mixture is fed downstream, and combined and mixed with aqueous alkaline solution feed 18 to control the pH and reequilibrate the phase separation occurring within drum 20 as described earlier. As also described earlier, a portion of the bottom aqueous salt phase is purged from drum 20 as aqueous salt phase purge 24, while the remaining aqueous salt phase exits drum 20 to heat treatment vessel 28 as neutralized aqueous salt phase stream 26. The aqueous salt phase stream will continue recirculating from drum 20 to heat treatment vessel 28 via neutralized aqueous salt phase feed 26, and back to drum 20 via aqueous salt phase feed 30 and cleavage product mixture feed 16. The circulation rate of these streams within the system is monitored to optimize the percent conversion of impurities to their water-soluble derivatives.

The method and system are further illustrated by the following non-limiting examples.

Example 1

In a continuous process cumene was oxidized to form CHP, and the resultant CHP was subjected to acid cleavage using a sulfuric acid catalyst feed 12 in reactor 14 to form cleavage product mixture feed 16.

Table 1 illustrates the cleavage product mixture components in wt. % based on the total weight of the CHP cleavage product mixture feed 16 as measured by gas chromatography.

| Component | Weight Percent (wt. %) |
| --- | --- |
| Phenol | 43.2% |
| Acetone | 39.0% |
| Cumene | 11.7% |
| Alphamethylstyrene | 3.1% |
| Water | 1.6% |
| Acetophenone | 0.7% |
| o,p-cumylphenol | 0.3% |
| Dimethylbenzyl alcohol | 0.1% |
| Hydroxyacetone | 0.12% |
| Acetaldehyde | 0.05% |
| Ducumyl peroxide | 0.01% |
| Acetic acid | 0.02% |
| Sulfuric acid | 0.03% |
| Mesityl oxide | 0.12% |

A 20 wt. % aqueous sodium hydroxide solution (stream 18) was added at a rate of 1,500 pounds per hour (lbs./hr) to the cleavage product mixture feed 16, having a feed rate of 200,000 lbs/hr, in an amount effective to neutralize the residual sulfuric acid present and provide a pH of 5–6 in neutralization drum 20. The resulting organic phase contained a hydroxyacetone concentration of 1250 parts per million (ppm), while the aqueous salt phase contained a 18 wt. % sodium sulfate solution having a hydroxyacetone concentration of 1107 ppm, an acetaldehyde concentration of 300 ppm, a phenol concentration of 5070 ppm, an acetone concentration of 9200 ppm, 0.5 wt. % sodium bisulfate, and 0.1 wt. % sodium acetate salts, as measured using an HP 5890 gas chromatograph and Dionex DX100 ion-chromatograph.

The aqueous salt phase was withdrawn from the bottom of the neutralizer drum 20, as a neutralized aqueous salt phase stream 26 having a pH of 4.5, and pumped into heat treatment vessel 28 at a rate of 500,000 lbs./hr. The heat treatment vessel 28 was maintained at a temperature of 300° C. and a pressure of 1240 psi for one hour without utilizing treating agents. The hydroxyacetone concentration in the resulting heat-treated aqueous salt phase stream 30 fed forward from the heat treatment vessel 28 was measured at less than 10 ppm, while the acetaldehyde concentration was measured at 30 ppm using a Dionex DX100 ion exclusion chromatograph. This represents a hydroxyacetone conversion of 99.9% using heat treatment alone. The phenol and acetone concentrations were unchanged at 5000 ppm and 9200 ppm, respectively, which indicates no product loss due to heat treatment.

Following recirculation at a rate of 500,000 lbs./hr of the heat-treated aqueous salt phase stream 30, and subsequent mixing and reequilibration with cleavage product mixture stream 16 in neutralizer drum 20, a qualitative analysis of neutralized cleavage product mixture stream 22 using gas chromatography analysis indicated a—hydroxyacetone concentration of 220 ppm, an acetaldehyde concentration of 90 ppm, and no 2MBF. This represents a hydroxyacetone conversion of 82.5%.

Example 2

A second trial was conducted utilizing the same raw materials and conditions used in Example 1, except that the heat treatment vessel 28 was operated at the following parameters: 200° C., 240 psi, and 1 hour residence time. The hydroxyacetone content in the heat-treated aqueous salt phase stream 30 was measured at 452 ppm, representing a hydroxyacetone conversion of 59%. Following recirculation of the heat-treated aqueous salt phase stream 30, and re-equilibration within neutralizer reactor 20, the hydroxyacetone concentration of neutralized cleavage product stream 22 was measured at 610 ppm, representing a hydroxyacetone conversion of 51.2%.

Example 3

A second trial was conducted utilizing the same raw materials and conditions used in Example 2, except that a 10 wt. % aqueous sodium sulfate solution was utilized. The hydroxyacetone concentration of the heat-treated aqueous salt phase stream 30, and neutralized cleavage product stream 22 (following recirculation) was measured at 495 ppm and 680 ppm, respectively.

Example 4

A third trial based upon Example 2 was conducted utilizing the same raw materials and conditions of Example 2, except that a 25 wt. % aqueous sodium sulfate solution was utilized. A qualitative analysis of heat-treated aqueous salt phase stream 30 and neutralized cleavage product stream 22 (following recirculation) indicated a hydroxyacetone concentration of 430 ppm and 588 ppm, respectively.

Example 5

A third trial based on Example 1 was conducted utilizing the same raw materials and conditions of Example 1, except that a synthetic aqueous solution containing 18.0 wt. % aqueous sodium sulfate solution having a 1477 ppm hydroxyacetone, 500 ppm phenol and 1000 ppm acetone was employed. The heat treatment vessel 28 was operated at the following parameters: 300° C., 1200 psi, 1 hour residence time, and pH of 5–7. A qualitative analysis of heat-treated aqueous salt phase stream 30 indicated a hydroxyacetone concentration of 115 ppm, representing a hydroxyacetone conversion of 92%. As noted in Example 1, both the phenol and acetone concentrations remain unchanged, thus indicating that heat treatment alone resulted in no product loss.

Example 6

A fourth trial based on Example 1 was conducted utilizing the same raw materials and conditions of Example 1, except that a synthetic aqueous solution containing 1000 ppm hydroxyacetone, 500 ppm phenol and 1000 ppm acetone was employed rather than an aqueous sodium salt solution. The heat treatment vessel 28 was operated at the following parameters: 300° C., 1250 psi, 1 hour residence time, and pH of 5–7. A qualitative analysis of heat-treated aqueous salt phase stream 30 indicated a hydroxyacetone concentration of 642 ppm, representing a hydroxyacetone conversion of 36% in the absence of sodium salts.

| Hydroxyacetone Concentration of Streams (parts per million) | | | | |
|---|---|---|---|---|
| Example No. | Stream 16 | Stream 26 | Stream 32 | Stream 22 |
| 1 | 1250 | 1107 | 10 | 480 |
| 2 | 1250 | 1107 | 452 | 610 |
| 3 | 1250 | 1107 | 495 | 680 |
| 4 | 1250 | 1107 | 430 | 588 |
| 5 | — | 1477 | 115 | — |
| 6 | — | 1000 | 642 | — |

The method and system for removing hydroxyacetone from a phenol-acetone mixture possesses several advantages such as reduced time, labor, equipment, treatment chemicals and costs associated with conventional purification methods, improving the quality of the final phenol product.

In particular, the inventive method and system employs heat alone rather than troublesome additional alkaline agents or condensation and conversion reactions. These surprisingly effective results obtained in the absence of any treatment additives is believed due to the discovery that the in-situ produced salts present in the sodium sulfate stream act as catalysts to promote the desired HA conversion reactions. There are accordingly none of the higher boiling point materials or 2-methybenzofuran as products, fouling of equipment due to overly acidic or alkaline process conditions, or fluctuations in pH, each of which may require complex systems to overcome. The inventive method and system thus alleviates the need for complex systems and expensive equipment, and requires a lower initial plant investment, as there is, except for an additional vessel, no requirement for special or additional equipment for multiple extraction and/or distillation steps.

The inventive method and system also eliminates or prevents the formation of heavy condensation products or high boiling point materials that foul downstream equipment and affect the quality of the final phenol products. Water-soluble oxidized derivatives of impurities such as hydroxyacetone and acetaldehyde are formed, separated in existing equilibration steps, and purged without employing additional distillation/extraction steps or equipment. As a result,

What is claimed is:

1. A method fur removing impurities from a cumene hydroperoxide cleavage product mixture, comprising:
   extracting, at a pH of about 2 to about 10, impurities from a first cumene hydroperoxide cleavage product mixture with an aqueous phase;
   neutralizing the aqueous phase to form an aqueous salt phase;
   heating the aqueous salt phase containing the impurities at a temperature or about 150 to about 350° Celsius for a time sufficient to form water-soluble derivatives of the impurities;
   extracting impurities in a second cumene hydroperoxide cleavage product mixture with the aqueous salt phase containing the water-soluble derivatives; and
   separating, from the extracted second cumene hydroperoxide cleavage product mixture, the aqueous salt phase containing the water-soluble derivatives from the first product mixture and the extracted impurities from the second product mixture.

2. The method of claim 1, wherein extraction of the second product mixture is in the presence of at least a portion of the first product mixture.

3. The method of claim 1, wherein greater than about 50 percent of the impurities are converted to the water-soluble derivatives.

4. The method of claim 1, wherein greater than about 80 percent of the impurities are converted to the water-soluble derivatives.

5. The method of claim 1, wherein greater than about 90 percent of the impurities are converted to the water-soluble derivatives.

6. The method of claim 1, wherein the impurities are mesityl oxide, acetaldehyde, hydroxyacetone, carbonyl-containing impurities, aldehyde-containing impurities, or a combination comprising at least one of the foregoing impurities.

7. The method of claim 1, wherein an aqueous alkaline solution is added to maintain a pH of about 3 to about 7 during heating.

8. The method of claim 1, wherein an aqueous alkaline solution is added to maintain a pH of about 5 to about 7 during heating.

9. The method of claim 1, wherein the aqueous salt phase comprises about 10 to about 30 weight percent sodium sulfate solution.

10. The method of claim 1, wherein the aqueous salt phase comprises about 10 to about 25 weight percent sodium sulfate solution.

11. The method of claim 1, wherein the temperature is about 200 to about 300° Celsius.

12. The method of claim 1, wherein a pressure of about 50 to about 1500 pounds per square inch is applied while heating the aqueous salt phase containing the impurities.

13. The method of claim 1, wherein a pressure of about 100 to about 1400 pounds per square inch is applied while heating the aqueous salt phase containing the impurities.

14. The method of claim 1, wherein a pressure of about 200 to about 1300 pounds per square inch is applied while heating the aqueous salt phase containing the impurities.

15. The method of claim 1, wherein the time is about 0.5 to about 1.5 hours.

16. A method for removing impurities from a cumene hydroperoxide cleavage product mixture, comprising:
   extracting at a pH of about 1 to about 10, impurities from a first cumene hydroperoxide cleavage product mixture with an aqueous phase;
   neutralizing the aqueous phase to form an aqueous salt phase;
   heating the aqueous salt phase containing impurities at a temperature of about 150 to about 350° Celsius and for a time of about 0.5 to about 1.5 hours under a pressure of about 50 to about 1500 pounds per square inch to form water-soluble derivatives of the impurities;
   extracting the impurities in a second cumene hydroperoxide cleavage product mixture with the aqueous salt phase containing the water-soluble derivatives; and
   separating from the extracted second cumene hydroperoxide cleavage product mixture the aqueous salt phase containing the water-soluble derivatives of the impurities from the first product mixture and the impurities from the second product mixture.

17. The method of claim 16, wherein an aqueous alkaline solution is added to maintain the pH at about 3 to about 7 during heating.

18. The method of claim 16, wherein the impurities ale mesityl oxide, acetaldehyde, hydroxyacetone, carbonyl-containing impurities, aldehyde-containing impurities, or a combination comprising at least one of the foregoing impurities.

19. The method of claim 16, wherein the aqueous salt phase comprises about 10 to about 30 weight percent sodium sulfate solution.

20. The method of claim 16, wherein the temperature is about 200 to about 300° C.

21. The method of claim 16, wherein the pressure is about 200 to about 1300 pounds per square inch.

22. A system for purifying a cumene hydroperoxide cleavage product mixture, comprising:
   means for extracting impurities from a first cumene hydroperoxide cleavage product mixture with an aqueous phase;
   means for neutralizing the aqueous phase to form an aqueous salt phase;
   means for heating the aqueous salt phase containing the impurities at a temperature of about 150 to about 350° Celsius for a time sufficient to form water-soluble derivatives of the impurities;
   means for extracting a second cumene hydroperoxide cleavage product mixture with the aqueous salt phase containing the water-soluble derivatives, wherein the means for extracting the first and second cumene hydroperoxide cleavage product mixtures may be the same or different; and
   means for separating from the extracted second cumene hydroperoxide cleavage product mixture tie aqueous salt phase containing the water-soluble derivatives from the first product mixture and the extracted impurities from the second product mixture.

23. A system for purifying a cumene hydroperoxide cleavage product mixture, comprising:
   a cumene hydroperoxide cleavage product mixture containing impurities feed and an aqueous alkaline solution feed in fluid communication with a neutralization drum having an aqueous salt phase outlet, wherein the aqueous salt phase outlet is in fluid communication with a heat treatment vessel having a heat-treated aqueous salt phase outlet, and further wherein the heat-treated aqueous salt phase outlet is in fluid communication with the cumene hydroperoxide cleavage product mixture containing impurities prior to the neutralization drum.

24. The system of claim 23, wherein the neutralization drum is in fluid communication with and serially disposed prior to the heat treatment vessel.

25. The system of claim 23, wherein the neutralization drum has an aqueous salt phase purge outlet and a neutralized cumene hydroperoxide cleavage product mixture outlet.

26. The system of claim 23, wherein the impurities are mesityl oxide, acetaldehyde, hydroxyacetone, carbonyl-containing impurities, aldehyde-containing impurities, or a combination comprising at least one of the foregoing impurities.

* * * * *